(12) United States Patent
Henon et al.

(10) Patent No.: US 10,150,119 B2
(45) Date of Patent: Dec. 11, 2018

(54) ROTARY SAMPLING VALVE AND DEVICE EQUIPPED WITH SUCH A VALVE

(71) Applicant: HORIBA ABX SAS, Montpellier (FR)

(72) Inventors: Nathalie Henon, Fons-Outre-Gardon (FR); Florent Beauducel, Montpellier (FR)

(73) Assignee: HORIBA ABX SAS, Montpellier (FR)

( * ) Notice: Subject to any disclaimer, the term of this patent is extended or adjusted under 35 U.S.C. 154(b) by 200 days.

(21) Appl. No.: 15/121,727

(22) PCT Filed: Feb. 20, 2015

(86) PCT No.: PCT/EP2015/053632
§ 371 (c)(1),
(2) Date: Aug. 25, 2016

(87) PCT Pub. No.: WO2015/128262
PCT Pub. Date: Sep. 3, 2015

(65) Prior Publication Data
US 2016/0361718 A1 Dec. 15, 2016

(30) Foreign Application Priority Data
Feb. 28, 2014 (FR) ..................................... 14 51635

(51) Int. Cl.
*B01L 3/00* (2006.01)
*F16K 11/074* (2006.01)
(Continued)

(52) U.S. Cl.
CPC ............ *B01L 3/567* (2013.01); *F16K 11/074* (2013.01); *F16K 11/166* (2013.01); *G01N 1/10* (2013.01);
(Continued)

(58) Field of Classification Search
CPC ...................................................... B01L 3/567
See application file for complete search history.

(56) References Cited

U.S. PATENT DOCUMENTS

| 4,726,237 A | * | 2/1988 | Yung ................... G01N 35/1097 73/863.73 |
| 5,089,234 A | * | 2/1992 | Preston .............. G01N 35/1097 137/382 |
| 6,662,826 B1 | * | 12/2003 | Kokawa ................ F16K 11/074 137/597 |

FOREIGN PATENT DOCUMENTS

FR 2924804 A1 6/2009

OTHER PUBLICATIONS

International Search Report issued in International Patent Application No. PCT/EP2015/053632 dated Jun. 11, 2015.

* cited by examiner

*Primary Examiner* — Paul West
*Assistant Examiner* — Mark A Shabman
(74) *Attorney, Agent, or Firm* — Arent Fox LLP

(57) ABSTRACT

The invention relates to a sampling valve and to a device equipped with such a valve notably allowing haematology measurements to be taken from a blood sample. The valve comprise two external parts, one internal part clamped between said external parts, and means for regulating the relative angular position of these parts about an axis of rotation. The internal part has opposite surfaces pressing in a sealed and sliding manner against adjacent surfaces of the external parts. The external parts comprise orifices, loops and ducts, said loops and said ducts being arranged in such a way as to communicate selectively with orifices passing through the internal part. The valve parts have no aliquot return groove or recess or labyrinth, thereby eliminating regions of turbulence. The valve is characterized in that two (Continued)

of the parts are able to rotate about the axis of rotation with respect to one of the said parts which is stationary, the rotary parts preferably being the external parts. The sampling valve also makes it possible to form calibrated volumes of a sample taken in the loops and/or the orifices of the internal part.

21 Claims, 5 Drawing Sheets

(51) Int. Cl.
    *F16K 11/16*     (2006.01)
    *G01N 35/10*     (2006.01)
    *G01N 1/10*     (2006.01)

(52) U.S. Cl.
    CPC .. *G01N 35/1097* (2013.01); *B01L 2400/0622* (2013.01); *B01L 2400/0644* (2013.01)

ROTARY SAMPLING VALVE AND DEVICE EQUIPPED WITH SUCH A VALVE

CROSS REFERENCE TO RELATED APPLICATION

This application is a 35 U.S.C. 371 National Phase of PCT Application No. PCT/EP2015/053632 filed Feb. 20, 2015, which claims priority to French Patent application Ser. No. 14/51,635 filed Feb. 28, 2014. The disclosure of these prior applications are hereby incorporated in their entirety by reference.

The present invention relates to a sampling valve and to a device equipped with such a valve, for example, but nonlimitingly, to a device for taking hematological and/or biochemical measurements from a biological sample.

Prior Art

Taking hematological and/or biochemical measurements using machines entails sampling the biological sample, for example the blood sample taken from patients. Sampling makes it possible to calibrate volumes of blood, referred to as aliquots. These aliquots are then mixed with various reagents to make it possible to reveal the constituents of the blood during analysis. The volumes of blood need to be calibrated accurately and repeatably in order to make the measurements reliable.

Several types of device for creating the aliquots are known, notably sampling valves.

A sampling valve can operate in isolation or can be incorporated into an analysis machine.

Automated analysis machines fitted with such valves allow operation at high rates, for example of the order of one measurement per minute.

The known sampling valves typically allow a biological sample to be split up in loops arranged on external parts that are stationary relative to an internal part that is capable of rotational movement. Mention may be made for example of documents WO 90/07702. WO 2004/034034 or U.S. Pat. No. 4,948,565.

Typically, the volumes of blood are calibrated either in loops or in chambers situated in a part.

The mixtures of aliquots of blood with reagents are typically transferred to outlet ducts by flowing in orifices and grooves formed in a part.

The presence of grooves results in the sampling valve becoming fouled, clogged and jammed.

In addition, the rotational drive of rotary parts is typically achieved using a stepping motor or a screw transmission stopped without a solid end-stop, resulting in a risk of loss of positioning of the relative angular position of the parts.

The parts of the known valves are clamped against one another in order to seal them. In addition, the unilateral rotation of the internal part is accompanied by a significant unbalanced force against the end stop which becomes degraded over the course of time. This contributes to the risk of loss of adjustment.

These disadvantages entail regular maintenance operations and complex adjustments which increase the operating and manufacturing costs.

It is a key objective of the present invention to alleviate all or some of the disadvantages of the sampling valves of the prior art.

It is another objective of the present invention to propose a sampling valve that simultaneously creates micro-aliquots of different volumes.

Yet another objective of the present invention is to propose a sampling valve with rotary elements that makes it possible to simplify the networks of loops, ducts and capillaries.

Another objective of the present invention is to propose a sampling valve that allows uniform and repeatable clamping of its elements.

Another objective of the present invention is to propose a sampling valve that evenly distributes the forces of rotation of its elements.

Yet another objective of the present invention is to propose a sampling valve that prevents any loss of positioning.

SUMMARY OF THE INVENTION

These objectives are achieved using a sampling valve which, according to a first aspect of the invention, comprises two external parts, one internal part clamped between said external parts, and means for adjusting the relative angular position of said parts about an axis of rotation, said internal part having opposite surfaces bearing in a fluid tight and sliding fashion against adjacent surfaces of said external parts, said external parts comprising orifices, loops and ducts, said loops and said ducts being configured to communicate selectively with orifices passing through said internal part, characterized in that:

two of said parts are able to rotate about said axis of rotation with respect to the one of said parts which is stationary, in particular, in embodiments in which the two parts able to rotate about the axis of rotation are the two external parts.

The mobility of two parts rather than just one allows various advantages to be afforded according to the embodiments and the practical situations encountered.

It is possible to create more functional states in which the two rotary parts are against end stops, and therefore without any problems of adjustment.

The rotation of two external parts offers the advantage of distributing the mechanical forces applied to the parts of the valve. In particular, simultaneous actuation of the external parts in opposite directions of rotation more or less cancels out the moments experienced by the internal part. Such a mechanical distribution also offers the advantage of optimizing the sealing of the valve. Furthermore, the rotation of two external parts makes it possible to simplify the networks of loops, ducts and orifices of the valve, for example by decreasing the number of loops and of orifices, while at the same time making it possible to increase the number of possible functional configurations.

The rotational movement of the external parts, which support nozzles for the inlet and outlet of the fluids (e.g. aliquots of blood, reagents) circulating or stored in the valve, notably allows the inlets and outlets to be offset from one another, particularly in a dispensing state (see later).

Depending on the embodiments, the rotary parts of the valve according to the invention may:
  be actuated simultaneously,
  be actuated simultaneously in opposite directions of rotation,
  be actuated separately from one another.

Depending on the embodiments, the sampling valve is characterized in that:
  the angular position of the rotary parts is controlled by a linear actuator via transmission means which are engaged with said rotary parts at different points about the axis of rotation;

the transmission means preferably comprise a yoke of which a central part is connected to the linear actuator, said yoke preferably comprising two arms, each arm of said yoke being connected to a respective one of the rotary parts;

a first end of each arm is secured to a translationally mobile part of the linear actuator, the mobile part preferably being a piston, and a second end of each arm is engaged with just one of the rotary parts;

the second respective end of each arm of the yoke is engaged with a respective rotary part such that the yoke grips the rotary parts in such a way as to drive the rotary parts in rotation through a translational movement of the mobile part of the linear actuator;

for preference, the points of connection between the transmission means and the rotary parts comprise a notch at the periphery of at least one of said rotary parts;

the periphery of the one of the parts comprises a recess allowing axial extraction without interference with the transmission means;

the actuator comprises a pneumatic piston;

in particular, when the rotation means comprise the aforementioned yoke, the pneumatic piston or other linear actuator is preferably mounted radially with respect to the axis of rotation;

in at least one of the relative angular positions, end-stop means define the angular position of the rotary parts;

the end-stop means comprise an end-stop element which extends axially into ports passing through the rotary parts with an angular clearance about the axis of rotation;

it comprises a compression system causing the parts to press axially together.

Actuation of the rotary parts of the valve by a linear actuator such as a pneumatic piston and, in embodiments in which a several angular positions of these rotary parts are afforded by a mechanical end stop makes it possible to avoid any risk of loss of positioning while at the same time allowing the use of a single actuator. Creating axial clamping using an axial compression system, with the clamping calibrated for example by a spring, allows the parts of the valve to be clamped uniformly and repeatably.

It is advantageous for the parts to have end stops relative to one another as far as their relative angular position is concerned, at least in some of the functional states, preferably in all of the functional states.

Hereinafter, a "valve of the specified type" refers to a sampling valve comprising two external parts, one internal part clamped between said external parts, and means for adjusting the relative angular position of said parts about an axis of rotation, said internal part having opposite surfaces bearing in a fluid tight and sliding fashion against adjacent surfaces of said external parts, said external parts comprising orifices, loops and ducts, said loops and said ducts being configured to communicate selectively with orifices passing through said internal part.

According to a second aspect of the invention, in a valve of the specified type, particularly but nonlimitingly in accordance with the first aspect, in which a relative rotation of the parts from a functional sample-withdrawing state isolates calibrated volumes of withdrawn liquid and then, when a functional dispensing state is reached, places these calibrated volumes in communication with dispensing circuits, the valve is characterized in that some of said calibrated volumes are defined in one or several loops and calibrated by the capacity of said one or several loops and other calibrated volumes are defined in one or several orifices of the internal part and calibrated by the capacity of said one or several orifices of said internal part.

In a first embodiment according to a third aspect of the invention, in a valve of the specified type, notably in accordance with the first aspect, the valve is characterized in that:

the orifices, the loops and the ducts of the external parts, and the orifices passing through the internal part are configured so as to define, through their relative angular positions, two distinct functional states:

a sample-withdrawing state or rinsing state, in which several of said loops are connected, by several of said orifices of said internal part and several of said orifices of said external parts, to at least one inlet duct and to at least one outlet duct, at least one dispensing state, in which a series of loops are sampling loops of calibrated volume and are connected, each one separately, by several of said orifices of said internal part and several of said orifices of said external parts, to at least one inlet duct and to at least one outlet duct;

or in that the orifices, the loops and the ducts of the external parts, and the orifices passing through the internal part are configured so as to define, through their relative angular positions, two distinct functional states:

a sample-withdrawing state or rinsing state, in which several of said loops are connected, by several of said orifices of said internal part and several of said orifices of said external parts, to at least one inlet duct and to at least one outlet duct, a dispensing state, in which at least one of said orifices of said internal part is a sampling chamber of calibrated volume and is directly connected, via orifices of said external parts, to at least one inlet duct and to at least one outlet duct.

According to these second and third aspects of the invention, and particularly in the embodiment which has just been explained, the aliquots may be formed either in the loops or in the chambers created by orifices of the internal part, or simultaneously in these loops and in these chambers. The volumes thus created are thus able to meet different calibration criteria according to the type of analysis to be carried out. That therefore makes it possible to combine analyses using for example volumes taken from the loops and microvolumes taken from chambers. Such an embodiment also makes it possible to optimize diluent and reagent consumption.

In addition, a valve created according to such an embodiment makes it possible to dispense with any grooves for communication between the loops, thereby limiting the risks of clogging and fouling.

In a second embodiment according to the third aspect of the invention, the orifices, the loops and the ducts of the external parts, and the orifices passing through the internal part are configured so as also to define, through their relative angular position:

a secondary dispensing state in which a second series of said loops are sampling loops of calibrated volume, and are connected, each one separately, by several of said orifices of said internal part and several of said orifices of said external parts, to at least one inlet duct and to at least one outlet duct; or a secondary dispensing state directly connecting at least one of said orifices of said internal part, via orifices of said external parts, to at least one inlet duct and to at least one outlet duct, said at least one of said orifices of said internal part being a sampling chamber of calibrated volume.

For preference, such a valve is characterized in that the external parts are actuated selectively so that:

said external parts move in opposite directions of rotation; or one of said external parts moves in a direction of rotation about the axis of rotation and the other of said external parts does not move in rotation about said axis of rotation.

A valve according to this second embodiment according to the third aspect of the invention makes it possible to keep at least one loop in reserve and/or at least one chamber in reserve in the internal part making it possible to perform an additional verification measurement without repeating the withdrawal of a sample.

This advantage is of particular relevance when the sampling valve is contained for example in an analysis machine that allows high sampling rates.

In a third embodiment according to the third aspect of the invention, the orifices, the loops and the ducts of the external parts, and the orifices passing through the internal part are configured so as to define, through their relative angular positions, a fourth functional state, namely, in addition to the three functional states of the second embodiment, a secondary sample-withdrawing state or secondary rinsing state in which several of said loops, some of which are common to said loops of said primary sample-withdrawing state, are connected, by several of said orifices of said internal part and several of said orifices of said external parts, to at least one inlet duct and to at least one outlet duct.

For preference, such a valve is characterized in that the external parts are actuated selectively so that:

said external parts move in the same direction of rotation; or said external parts move in opposite directions of rotation; or one of said external parts moves in a direction of rotation about the axis of rotation and the other of said external parts does not move in rotation about said axis of rotation.

A valve according to this third embodiment according to the third aspect of the invention makes it possible to form two sample-withdrawing circuits operating in parallel within the same valve.

Furthermore, it makes it possible to perform an additional verification measurement without repeating the withdrawal of a sample.

These advantages are of particular relevance when the sampling valve is contained for example in an analysis machine that allows high sampling rates.

For preference, in all of the embodiments of the third aspect, at least one of said dispensing states also directly connects at least one of the orifices of the internal part, via orifices of the external parts, to at least one inlet duct and to at least one outlet duct, said at least one of said orifices of said internal part being a sampling chamber of calibrated volume.

The valve according to the invention makes it possible to dispense with any groove or hollow formed in one or more parts of the valve. This then avoids the creation of regions of turbulence and consequently avoids fouling and clogging of the valve.

A sampling valve is highly sensitive to disturbances in the flows of fluid flowing through it. The absence of regions of turbulence is of prime importance to not generate false results when using the valve. For this reason, it is particularly advantageous for the valve not to contain any regions of turbulence such as hollows (or chicanes that send the aliquot back in the opposite direction) in the ducts through which typically lysed blood (burst cells) circulates, because the proteins that this lysed blood contains become caught in the corners and may become permanently deposited, leading for example to fouling or a re-release of particles that are foreign to the content of aliquots.

A sampling valve is also highly sensitive to variations in the diameter of the internal ducts (pressure drops). It is thus necessary to avoid any variation in diameter as accomplished by hollows (chicanes that send the aliquot back) in the ducts through which the reagents circulate because a reagent out gassing phenomenon occurs in the regions of reduced pressure, leading to the formation of microbubbles (e.g. a dummy count of ghost cells).

In addition, such a valve needs to be perfectly cleaned out between uses, typically between two cycles of analyzing blood from different patients. It is thus necessary to avoid regions in which the speed of a fluid cancels out, such as regions achieved through the presence of hollows (chicanes that send the aliquot back), because rinsing is ineffective or prevented in such regions.

It would seem that the sampling valve according to the invention is able to meet these requirements. In order to avoid hollows and regions of great turbulence, the direction in which the fluid or fluids circulating in the valve circulate are always through-directions (i.e. no "about-turns" using hollows), particularly in the internal part. Thus, the fluid or fluids circulating or contained in the internal part of the valve circulate or are contained in orifices passing through this internal part, these orifices preferably being cylindrical orifices and preferably being perpendicular to said opposite surfaces pressing in a fluid tight and sliding manner against the adjacent surfaces of the external parts.

Some applications require the creation of aliquots of a small volume of blood, for example less than 5 µl of blood, and of other aliquots with a volume of blood of the order of ten microliters or so. Implementation of such applications presents technical requirements notably in terms of the overall size or dimensions of the valve.

The valve according to the invention is able to meet such technical requirements through the creation of microdrillings in the internal part and a dimensioning of this internal part that gives it a small thickness, for example of the order of a few millimeters, the thickness of the internal part preferably being less than 3 mm, preferably less than 2.5 mm. For preference, the internal part is substantially cylindrical and its diameter is less than 40 mm, preferably less than 30 mm. For preference, the volume formed by said microdrillings is less than 1 µl, preferably less than 0.5 µl. Because such dimensioning weakens this internal part, particularly when this internal part is made of ceramic, the solution that involves rotating the external parts is particularly advantageous.

For preference, the thickness of the external parts is less than 6 mm, preferably less than 4.5 mm. For preference, the external parts are substantially cylindrical and their diameter is less than 45 mm, preferably less than 35 mm.

Furthermore, the valve according to the invention also makes it possible partly to satisfy the aforementioned technical requirements through the creation of greater volumes of blood, for example of the order of 10 microliters or so, in the sampling loops. For preference, sampling loops have an inside diameter less than 2 mm, preferably less than 1 mm.

For preference, the volume formed by at least part of the sampling loops is less than 35 µl, preferably less than 25 µl. In order to comply with the manufacturing tolerances on the loops able to calibrate accurately the aliquots formed therein, the sampling loops are typically made using metal tubing, plastic tubing being inappropriate.

In one embodiment of the sampling valve according to the invention, use is made simultaneously of human blood and at least four different reagents having different properties typically prejudicial at once to the blood samples, to the other reagents and/or to the sampling valve. All the distributions take place simultaneously. In particular, all the volumes of blood are withdrawn in a single go, that is to say in a single relative position of the moving parts that corresponds to the sample-withdrawing state. In another position, a step of calibrating, distributing and mixing these aliquots of blood with the appropriate volume of each of the respective reagents is then performed.

Causing the external parts to effect a rotary movement makes it possible to avoid jamming and have a load distribution that is the same whatever the relative position of the parts.

Sampling and distribution are performed in a very short space of time, of the order of 1 second, and it is important that the positioning of the parts of the valve be accurate (to the order of one micron) and repeatable. In addition, in order to limit maintenance operations and increase the life of the valve (limiting the risks of loss of power and of breakdown), it is necessary for the moving parts to reach the various relative positions as simply as possible.

In this respect, the valve according to the invention is able advantageously to meet such requirements, particularly through the use of a linear actuator associated with a yoke which drives each external part at the same time and in opposite directions about a single axis of rotation, or alternatively through the presence of a single spring in order to achieve uniform pressure of the valve parts against one another, or even through the single and robust positioning end-stop effect that limits losses of positioning.

For preference, the valve parts contain ceramic. Ceramic means that the valve can be rendered neutral from a thermal and chemical standpoint so as to avoid corrosion or contamination through the re-release of particles. Ceramic also makes it possible to ensure good flatness of the parts on the surfaces that place two given parts in contact with one another, and very low surface roughness.

The invention also relates to a device for analyzing biological parameters using at least one sampling valve according to the first or the second aspect of the invention, and in each of the embodiments that have just been explained.

LIST OF FIGURES AND DESCRIPTION OF EMBODIMENTS

Other specifics and advantages of the invention will become apparent from the detailed description of entirely nonlimiting embodiments and from the attached drawings in which.

Figures 1, 2:
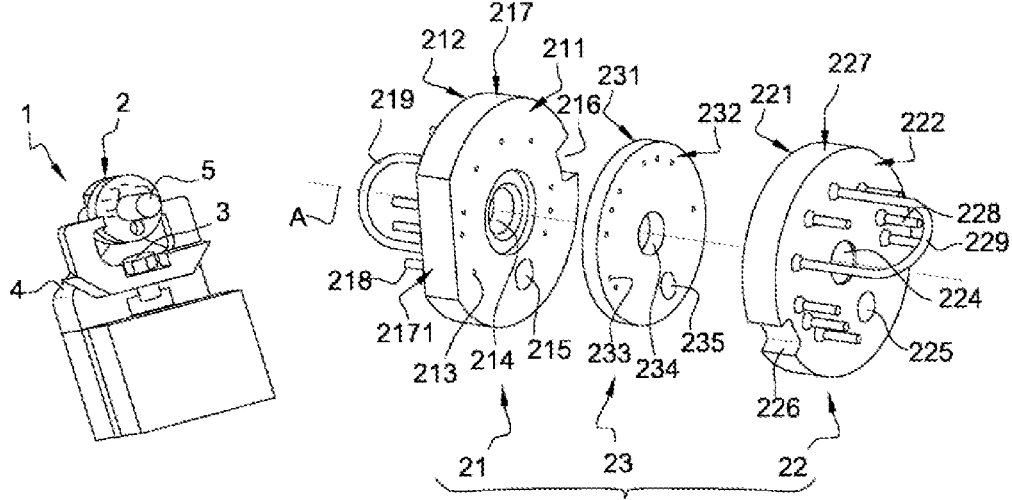
FIG. 1 is a perspective view of a sampling valve according to one preferred embodiment of the invention.
FIG. 2 is an exploded perspective view of a sampling assembly, showing the parts of the valve of FIG. 1, according to one preferred embodiment of the invention.
Figures 3, 4:
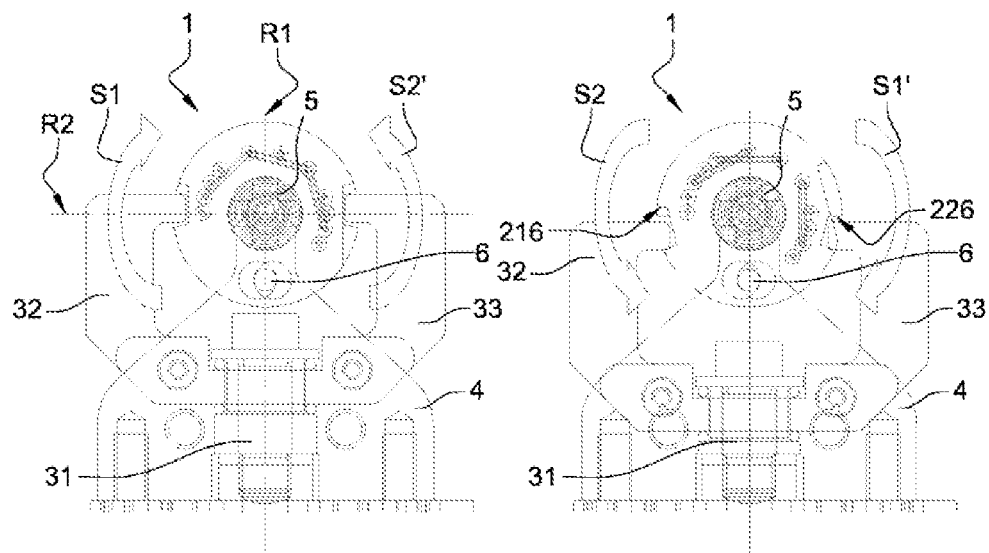
FIGS. 3 and 4 are schematic depictions of the valve of FIG. 1 in two distinct functional states.
Figure 5:
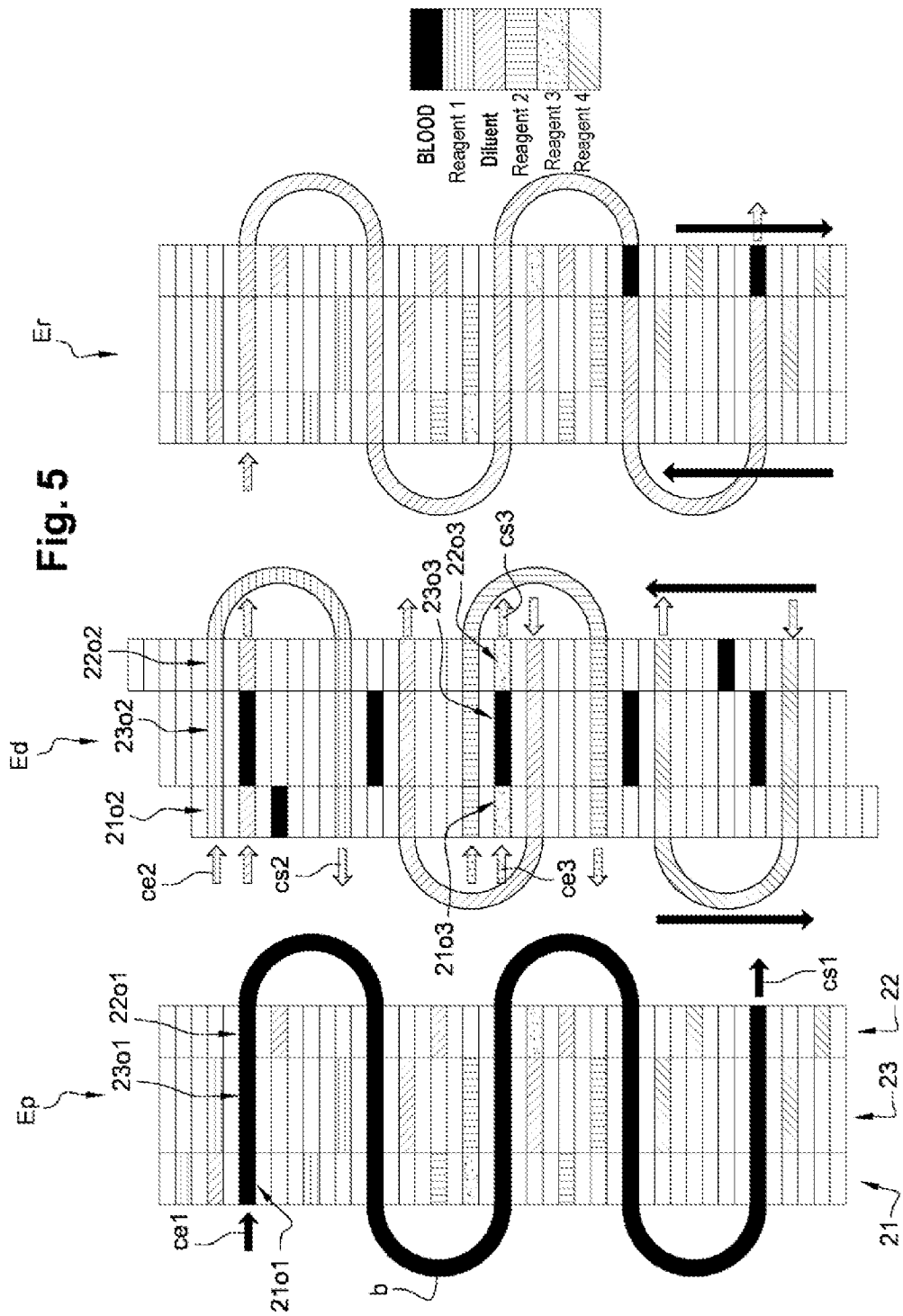
Figure 6:
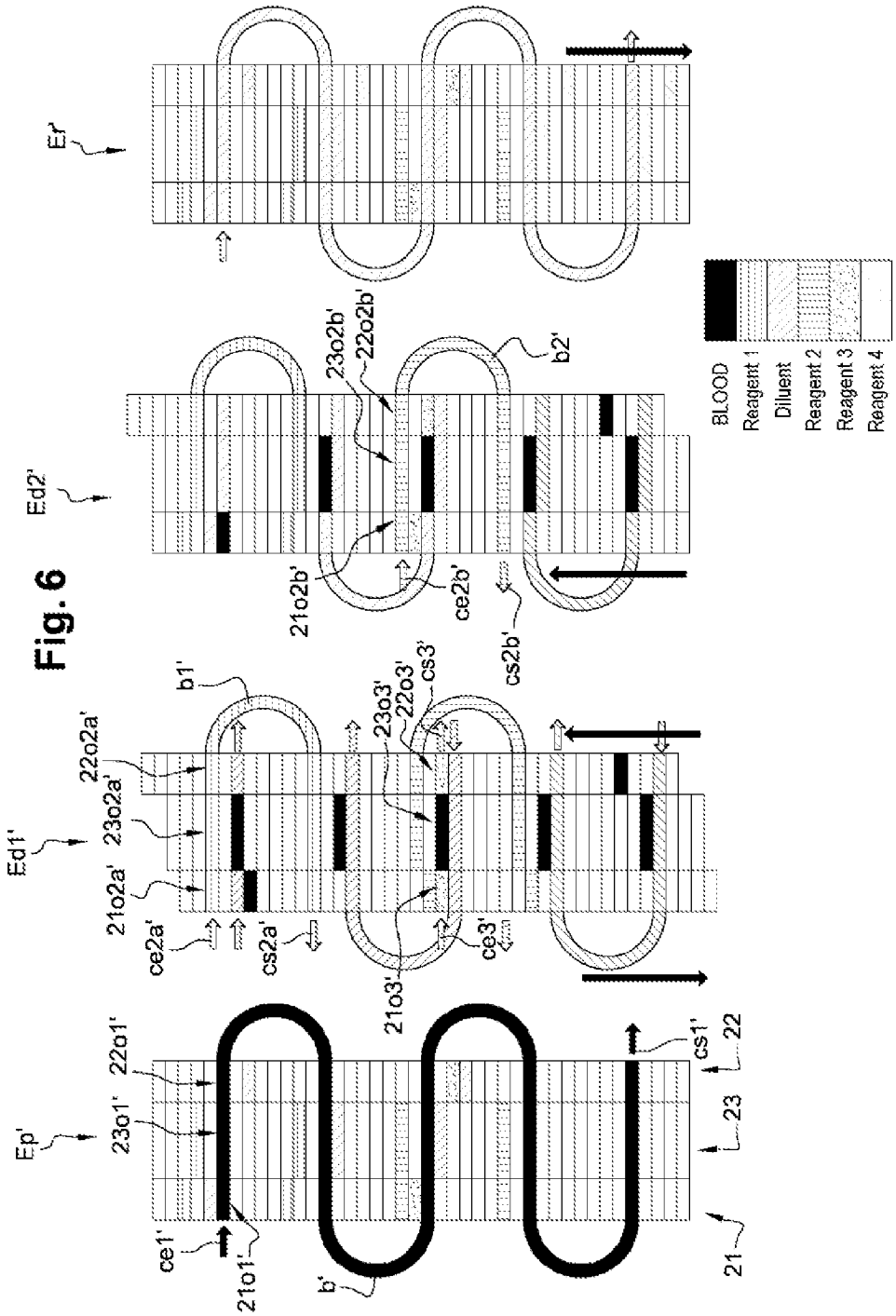
Figure 7:
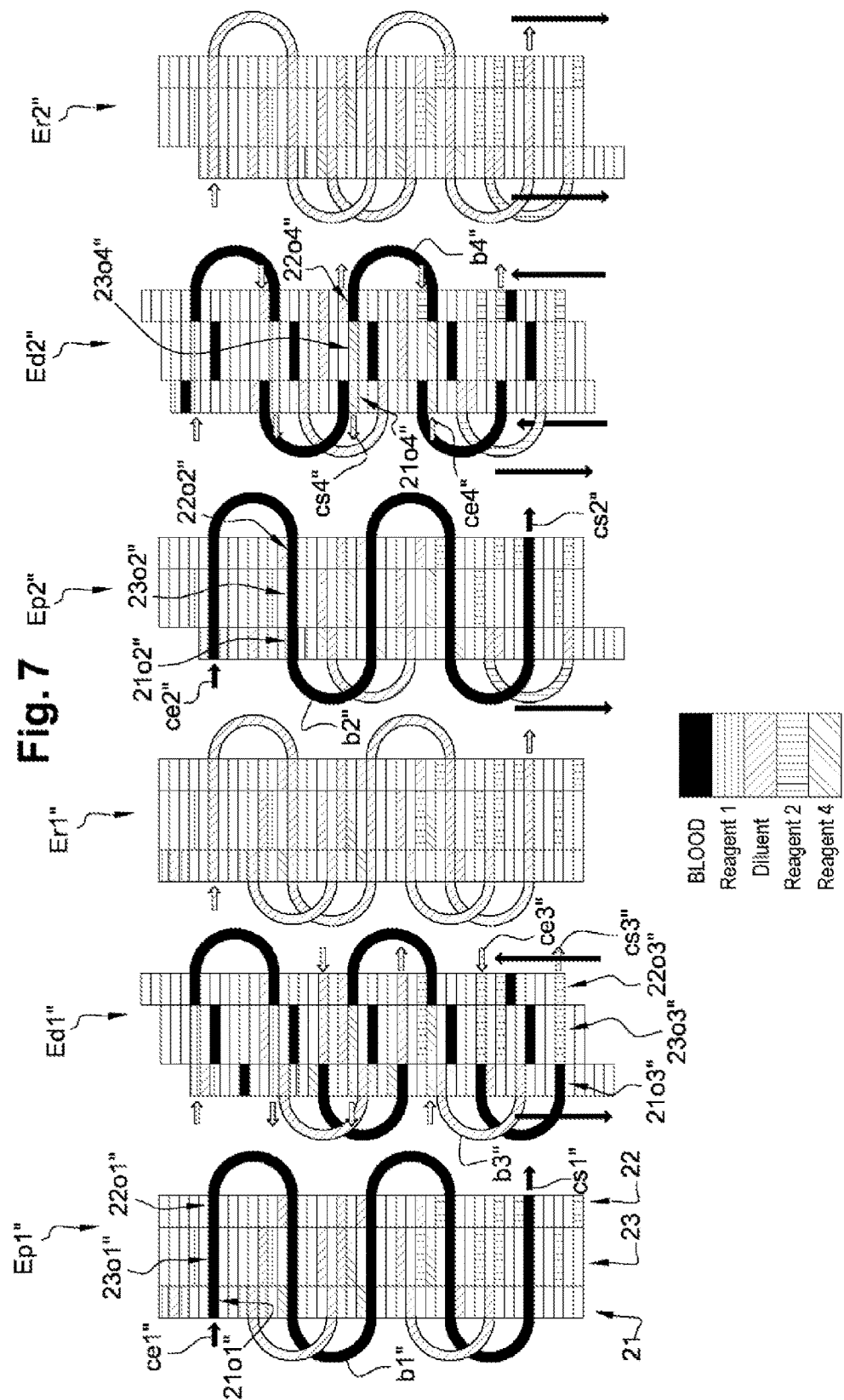
Figure 8:
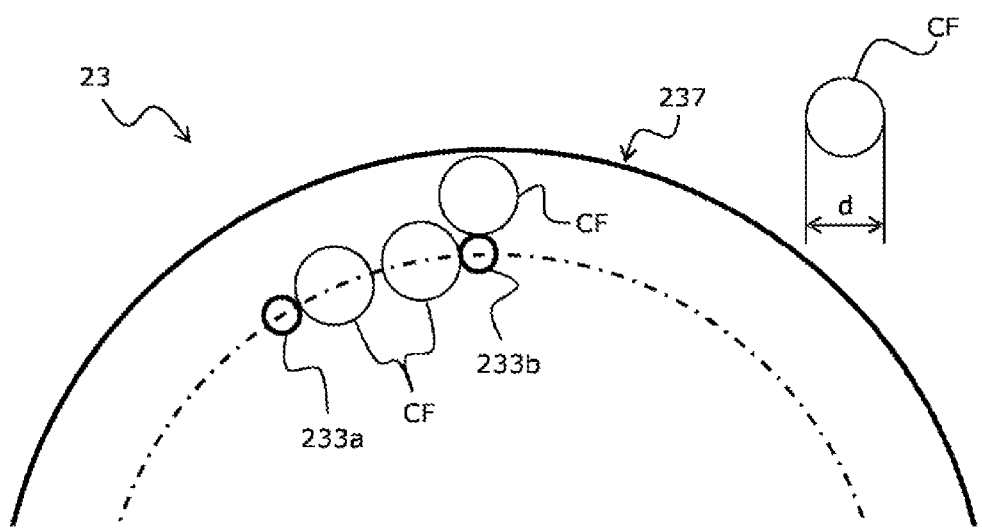

a sample-withdrawing or rinsing state in FIG. 3, a dispensing state in FIG. 4;

FIGS. 5 to 7 each illustrate the operation of the sampling valve in its various functional states, according to three other embodiments of the invention;

FIG. 8 is a partial view of a part of the valve of FIG. 1 and depicts a sealing distance.

Because these embodiments are entirely nonlimiting it is notably possible to conceive of alternative forms of the invention that comprise only a selection of the features described hereinafter, in isolation from the other features described, if this selection of features is enough to confer a technical advantage or to differentiate the invention from the prior art.

The sampling valve 1 depicted in FIGS. 1 to 4 comprises a sampling assembly 2, an actuator 3 and a support 4.

The sampling assembly 2 comprises two parts 21, 22 capable of rotational movement about a common axis A, referred to as rotary parts, with respect to a part 23 that is stationary relative to the support 4. In this embodiment, the rotary parts 21, 22 and the stationary part 23 have the overall shape of disks. They are stacked along the axis A and are in contact in pairs on their mutual-contact faces 211, 221, 231, 232 which are planar and perpendicular to the axis A.

The rotary parts are the two external parts 21 and 22 positioned one on each side of the internal part 23.

The internal part 23 has, passing through it, orifices 233 which connect the contact surfaces 231, 232 to one another.

The external parts 21, 22 bear sampling loops 219, 229 and dispensing and discharge ducts 218, 228 fixed to their external face 212, 222. The loops 219, 229 each have two ends which open through the contact face 211, 221 onto at least two orifices 233 of the internal part 23. The ducts 218, 228 each have two ends of which one opens through the contact face 211, 221, onto at least one orifice 233 of the internal part 23.

The external parts 21, 22 and internal part 23 of the sampling assembly 2 comprise a central opening 214, 224, 234 to accommodate a clamping system 5, for example involving a spring. The clamping system 5 allows calibrated centralized clamping of the external parts 21, 22 and internal part 23 about the axis A of rotation of the external parts 21, 22. This clamping causes there to be, between the contact faces, enough pressure to seal the contact between the contact faces 211, 231 and 221, 232, insofar as withdrawn fluid or analysis fluid cannot infiltrate between the contact faces in any significant quantity. However, the contact faces have a surface roughness that is low enough to allow relative sliding between the contact faces in order to allow the mutual rotation of the parts. This low surface roughness is favorable to achieving the desired sealing.

The external parts 21, 22 of the sampling assembly 2 further comprise an eccentric opening 215, 225, produced as circular in this embodiment. The internal part 23 also comprises an eccentric opening 235, for example oblong in shape in a first radial direction R1 of the sampling assembly 2. A shaft 6 of cylindrical shape and of a diameter substantially identical to the shortest width of the eccentric opening 235 of the internal part 23 passes through the eccentric openings 215, 225, 235 of the external parts 21, 22 and internal part 23. The eccentric openings 215, 225 have, about the axis A, a circumferential dimension greater than the diameter of the shaft 6, for example, but nonrestrictively, a factor of two times greater, so that the shaft can be in contact only along an edge face of the housing formed by each of the eccentric orifices 215, 225 of the external parts 21, 22.

Furthermore, the shaft 6 is stationary with respect to the stationary support 4.

Such an assembly makes it possible, when the external parts 21, 22 and internal part 23 are brought into contact and clamped by the clamping system 5, for the internal part 23 to be immobilized in terms of rotation relative to the support 4 by the shaft 6, by reason of the diameter of the shaft 6 being substantially identical to the width of the eccentric opening 235 of the internal part 23. In addition, the movement of the external parts 21, 22 about the axis of rotation A is limited in each of the two directions of rotation S1, S2 (part 22) or S1', S2' (part 21) by the shaft 6 which comes into abutment with the housing of the eccentric orifices 215, 225. Thus, in each functional state, the three parts 21, 22, 23 are in abutment against one and the same reference surface end stop formed by the lateral wall of the shaft 6.

It should be noted that this configuration is particularly advantageous for positioning the rotary parts 21, 22 in a repeatable relative angular position.

In the embodiment depicted in FIGS. 1, 3 and 4, the actuator 3 is a linear actuator comprising a piston 31 translationally moved in a radial direction with respect to the axis of rotation A, in this instance the radial direction R1. In the example, this direction is vertical. The actuator is positioned underneath the parts 21, 22, 23.

The piston 31 is secured to an actuating yoke comprising two arms 32, 33 of which the ends are in engagement with notches 216, 226 formed in the flanks 217, 227 of the rotary parts 21, 22. In a preferred embodiment, the flanks 217, 227 are situated one on each side of the direction of actuation of the actuator 3.

With reference to FIG. 3, the movement of the piston 31 and of the yoke 32, 33 toward the sampling assembly (toward the top of the figure) produces a rotational movement about the axis A in a first direction S1 of the external part 22 and in a second direction S2', the opposite of the first direction S1, of the external part 21.

With reference to FIG. 4, the movement of the piston 31 and of the yoke 32, 33 in the opposite direction to that of the sampling assembly 2 (toward the bottom of the figure) produces a rotational movement about the axis A in the first direction S1' of the external part 21 and in the second direction S2' of the external part 22.

Whatever the direction in which the piston 31 moves, the amplitude of this movement is determined by the circumferential clearance about the axis A of the shaft 6 in the eccentric orifices 215, 225 of the external parts 21, 22.

This embodiment offers the advantage of distributing the forces of rotation over the external parts 21, 22 thereby making it possible to reduce the risks of jamming. In addition, this embodiment allows the two external parts 21, 22 to be actuated using one single actuator 3 operating with a simple piston 31 moved translationally, thereby both reducing the size and the costs of manufacture and making the manufacturing and maintenance operations easier.

This embodiment is also particularly advantageous in that in each of the two functional states, the three parts 21, 22, 23 are pressed into abutment against the shaft 6 acting as an end stop, or in other words against a common reference surface, thereby avoiding the risk of the external parts 21, 22 losing their positioning.

Further aspects of the invention which are compatible with several combinations of embodiment of the first aspect of the invention and which notably relate to the way in which the networks of loops 219, 229, of ducts 218, 228 and of orifices 213, 223, 233 of the parts 21, 22, 23 are organized relative to relative angular positions of the rotary parts 21, 22 will now be described.

Three embodiments of the invention will now be described in particular with reference to FIGS. 5 to 7.

FIGS. 5 to 7 illustrate the operation of the sampling valve in various functional states. For each functional state the parts 21, 22, 23 have been shown rolled out so that their relative angular position can be seen in the form of a relative portion in the vertical direction.

Furthermore, each part is subdivided in the circumferential direction (which is vertical in FIGS. 5 to 7) into small elementary rectangles so that the relative angular position of the parts 21, 22, 23 can be seen schematically.

The series of small rectangles which are contained within each part in FIGS. 5 to 7 also illustrates how the loops, ducts and orifices of the parts 21, 22, 23 communicate with one another in each of the functional states depicted. Thus, certain small rectangles (for example $21o1$, $22o1$, $23o1$ in FIG. 5) represent orifices in the parts 21, 22, 23.

The embodiment of FIG. 5 comprises two distinct functional states: (1) a sample-withdrawing state Ep or rinsing state Er, and (2) a dispensing state Ed.

It can be seen in FIG. 5 that the sample-withdrawing state Ep or rinsing state Er is one and the same state because the relative angular position of the parts 21, 22, 23 is the same. In this particular instance, the parts 21, 22, 23 are depicted in an angular position referred to as a reference position illustrated by an alignment of the parts 21, 22, 23. The sample-withdrawing state Ep and the rinsing state Er are depicted separately in order to illustrate two possible uses of this functional state. In the sample-withdrawing state Ep, a liquid, for example a blood sample, is injected into an inlet duct ce1 and circulates as far as an outlet duct cs1, passing via loops b and orifices $22o1$, $22o1$, $22o3$ of the parts 21, 22, 23 which are all in series with one another to form a continuous and non-branched passage between the ducts ce1 and cs1. In the rinsing state Er, another liquid, for example a diluent, is injected into the same inlet duct and circulates through the same orifices and loops as far as the outlet duct allowing these orifices and loops to be cleaned out. In both instances, the injected liquid invades the entirety of the continuous passage formed between the ducts ce1 and cs1.

The dispensing state Ed depicted in FIG. 5 is a second functional state of the sampling valve according to the invention. This state is typically used to form aliquots of blood and to dispense these aliquots with various reagents so as to carry out analyses on the blood sample withdrawn.

It may be seen in FIG. 5 that the dispensing state Ed is obtained by a movement of the external parts 21, 22 in opposite directions and by identical amplitudes, in this instance visualized as the height of two small rectangles, with respect to the sample-withdrawing state Ep.

After the filling notably of the orifices $21o1$, $22o1$, $23o1$ and of the loops b in the sample-withdrawing state Ep, the relative rotary positioning of the external parts 21, 22 into the dispensing state Ed makes it possible to form aliquots of the withdrawn liquid in several or all of the loops b, referred to as sampling loops, and in the orifices $23o3$ of the part 23, which are referred to as sampling chambers. In order to dispense the sampled volumes of liquid in the sampling loops, reagents are inserted into the inlet ducts ce2 so as to drive the aliquots to circulate in the orifices $21o2$, $22o2$, $23o2$, which are aligned, of the parts 21, 22, 23 as far as the outlet ducts cs2. In order to dispense the sampled volumes of liquid in one or several sampling chambers $23o3$, one or several reagents are inserted into one or several inlet ducts ce3, so as to circulate in one or several orifices 21o3 and 22o3 aligned with the sampling chamber or chambers 23o3 as far as one or several outlet ducts cs3.

The creation of aliquots in the sampling loops and in the sampling chambers makes it possible to obtain two types of liquid-volume calibration and, for example, to carry out standard sampling in the loops and more accurate micro-sampling in the chambers.

The valve offers the advantage of allowing sampling using either both types of calibration or just one at a time.

The embodiment that has just been described is notably compatible with the feature of relative angular positioning of the external parts 21, 22 defined by end-stop means 6 from the first aspect of the invention.

In particular, the sample-withdrawing state Ep and rinsing state Er can be obtained by the state of the valve 1 depicted in FIG. 3 whereas the dispensing state Ed may be obtained by the state of the valve 1 depicted in FIG. 4 (see above for the description of these figures).

The embodiment of FIG. 6 comprises three distinct functional states: (1) a sample-withdrawing state Ep' or rinsing state Er', (2) a primary dispensing state Ed1', and (3) a secondary dispensing state Ed2'.

The operation and the principle of the sample-withdrawing state Ep' or rinsing state Er' of this embodiment are similar to those of the sample-withdrawing state Ep or rinsing state Er of the previous embodiment.

One particular feature of this embodiment has to do with the existence of two dispensing states Ed1', Ed2'. These dispensing states Ed1', Ed2' are based on the same principle of operation as the dispensing state Ed of the previous embodiment (see above). This embodiment, however, makes provision for two independent dispensing networks each having their own loops b1', b2' and/or sampling chambers 23o3'.

As FIG. 6 shows, each of the two dispensing states Ed1', Ed2' is associated with a relative angular position of the external parts 21, 22 which is obtained by a movement of different amplitude for each of these parts 21, 22.

In the primary dispensing state Ed1', the parts 21, 22 are moved in opposite directions with respect to the sample-withdrawing state Ep' and the amplitude of this movement can be visualized as the height of one small rectangle in the case of the part 21 and of two small rectangles in the case of the part 22.

In the secondary dispensing state Ed2', the rotary part is moved back to the reference position of the sample-withdrawing state Ep', namely by a value of one small rectangle in FIG. 6 with respect to the primary dispensing state Ed1'. By contrast, in the secondary dispensing state Ed2', the rotary part 22 is not moved with respect to the primary dispensing state Ed1'.

The configuration that has just been described makes it possible, in the secondary dispensing state Ed2', to use one or several sampling loops b2' and corresponding orifices 21o2b', 22o2b', 23o2b' and ducts ce2b', cs2b' and/or one or several sampling chambers and corresponding orifices and ducts not used in the primary dispensing state Ed1'.

Correspondingly, this configuration makes it possible, in the primary dispensing state Ed1', to use one or several sampling loops b1' and corresponding orifices 21o2a', 22o2a', 23o2a' and ducts ce2a', cs2a' and/or one or several sampling chambers 23o3' and corresponding orifices 21o3', 22o3' and ducts ce3', cs3' not used in the secondary dispensing state Ed2'.

The presence of two parallel dispensing states Ed1', Ed2' offers the notable advantage of being able to form aliquots referred to as reserve aliquots which may for example be used if the analyses performed during a first dispensing need to be supplemented. A second series of analyses can then be performed without having to make a second withdrawal.

The embodiment of FIG. 7 comprises four distinct functional states: (1) a primary sample-withdrawing state Ep1" or primary rinsing state Er1", (2) a secondary sample-withdrawing state Ep2" or secondary rinsing state Er2", (3) a primary dispensing state Ed1", and (4) a secondary dispensing state Ed2".

This embodiment is based on several principles which are similar to the two embodiments that have just been described. In particular, it makes provision for two dispensing states Ed1", Ed2" in respect of which reference may be made to the description of the dispensing states Ed1', Ed2' of the previous embodiment.

The combination of the primary sample-withdrawing state Ep1" or primary rinsing state Er1" and of the primary Ed1" and secondary Ed2" dispensing states relates to an embodiment similar to the previous embodiment.

One particular feature of this embodiment has to do with the existence of a second sample-withdrawing state Ep2" or rinsing state Er2" in parallel with the first sample-withdrawing state Ep1" or rinsing state Er1". After the withdrawal of the sample in the primary sample-withdrawing state Ep1", the filling of the loops b1" and orifices 21o1", 22o1", 23o1" via the ducts ce1", cs1" and the dispensing, one rotary part 21 is moved to configure the valve into the secondary sample-withdrawing state Ep2" so as to allow loops b2" and orifices 21o2", 22o2", 23o2" to be filled via ducts ce2", cs2".

As depicted in FIG. 7, one or several of the loops b1", b2" and one or several orifices 23o1", 23o2" differ between the two sample-withdrawing states Ep1", Ep2". Thus, rinsing will typically be performed in the primary rinsing state Er1" between the first withdrawal made in the primary sample-withdrawing state Ep11" and the second withdrawal made in the secondary sample-withdrawing state Ep2".

In the primary dispensing state Ed1", aliquots calibrated in sampling loops b3" and/or in sampling chambers are dispensed with reagents in the same way as in the previous embodiments.

Furthermore, the secondary dispensing state Ed2" makes it possible to conduct a new series of analyses using the aliquots withdrawn in the secondary sample-withdrawing state Ep2".

Thus, the sampling valve 1 comprises the two external parts 21, 22, the internal part 23 clamped between said external parts 21, 22 and the means 3 for adjusting the relative angular position of said parts 21, 22, 23 about the axis of rotation A, said internal part 23 having opposite surfaces 231, 232 bearing in a fluid tight and sliding fashion against adjacent surfaces 211, 221 of said external parts 21, 22, said external parts 21, 22 comprising orifices 213, loops 219, 229 and ducts 218, 228, said loops 219, 229 and said ducts 218, 228 being configured to communicate selectively with orifices 233 passing through said internal part 23. Two 21, 22, of said parts 21, 22, 23 are able to rotate about said axis of rotation A with respect to the one 23 of said parts 21, 22, 23 which is stationary.

An inter-orifice distance is defined as being, for all the orifices 213, 223, 233, the minimum distance between the outlines of two of these orifices 213, 223, 233 on a given part 21, 22, 23.

According to one advantageous feature, the orifices 213, 223, 233 of a given part 21, 22, 23 are spaced apart (on an opposite or adjacent surface of the part 21, 22, 23) by the inter-orifice distance at least.

The outline of each orifice 213, 223, 233 of a given part 21, 22, 23 is spaced apart (on an opposite or adjacent surface of the part 21, 22, 23) from the edge of the part 21, 22, 23 in which it is made by at least one orifice-edge distance.

A sealing distance "d" is defined such that the inter-orifice distance is preferably greater than twice this sealing distance and such that the orifice-edge distance is preferably greater than this sealing distance (see FIG. 8). The sealing distance is determined according to the perimeter (or diameter) of an orifice that is to be isolated and according to the pressure applied to this orifice by the fluid it contains. This sealing distance is preferably greater than 2 mm, preferably greater than 2.4 mm. These ranges of values for the sealing distance notably ensure good sealing of the valve for a valve fluid pressure of around 1.5 bar and an orifice diameter of less than 0.5 mm.

The sealing distance "d" is depicted in FIG. 8 by the diameter of an imaginary circle CF. FIG. 8 is a partial view of the internal part 23 on which are depicted two orifices 233a, 233b. Three imaginary circles CF are positioned tangentially with respect to these orifices 233a, 233b indicating that said inter-orifice distance and said orifice-edge distance (this edge of the part 23 bearing the reference 237) are greater than the sealing distance, namely than the diameter of the imaginary circle CF.

Such a feature means that each duct can be isolated, particularly during a change in position of the rotary parts 21, 22, for example from a sample-withdrawing position to a dispensing position. Thus, the sealing distance makes it possible to avoid leaks of liquid both in a given position of the rotary parts 21, 22 and while these rotary parts 21, 22 are turning.

One important advantage of the valve according to the invention is that it makes it possible to ensure correct operation without creating grooves or hollows (or chicanes that send aliquot back). The presence of hollows means that such hollows need to be rinsed out in each of the states described above. The absence of hollows on the other hand means that the rinsing can be carried out in one and only one of these states, thereby making it possible to simplify the hydraulic circuit. The rinsing can be performed in the position of the valve parts that corresponds to the sample-withdrawing state.

The valve according to the invention also allows the rinsing to be performed exhaustively and in a precise order from the least-corrosive reagent to the most-corrosive reagent.

The invention claimed is:

1. A sampling valve comprising two external parts, and one internal part clamped between said external parts wherein the external parts are rotatable about an axis of rotation (A), said internal part having opposite surfaces bearing in a fluid tight and sliding fashion against adjacent surfaces of said external parts, said external parts comprising a plurality of external orifices, loops and ducts, said loops and said ducts being configured to communicate selectively with internal orifices passing through said internal part, wherein the external and internal parts are configured so as to allow, through a relative rotation, a transition
   from a functional sample-withdrawing state, in which calibrated volumes of withdrawn liquid are isolated,
   to a functional dispensing state in which calibrated volumes are placed in communication with dispensing circuits,
   wherein some of said calibrated volumes are defined in one or several loops and calibrated by the capacity of said one or several loops and other calibrated volumes are defined in one or several orifices of the internal part and calibrated by the capacity of said one or several orifices of said internal part.

2. The sampling valve as claimed in claim 1, wherein the two parts able to rotate about the axis of rotation (A) are the two external parts.

3. The sampling valve as claimed in claim 1 wherein the rotary parts may be actuated simultaneously.

4. The sampling valve as claimed in claim 1, wherein the rotary parts may be actuated simultaneously in opposite directions of rotation.

5. The sampling valve as claimed in claim 1, wherein the angular position of the rotary parts is controlled by a linear actuator via a transmission which is engaged with said rotary parts at different points about the axis of rotation (A).

6. The sampling valve as claimed in claim 5, wherein the transmission comprises a yoke having a central part connected to the linear actuator, said yoke comprising two arms, wherein each arm of said yoke is connected to a respective one of the rotary parts.

7. The sampling valve as claimed in claim 6, wherein a first end of each arm is secured to a translationally mobile part of the linear actuator, and a second end of each arm is engaged with just one of the rotary parts.

8. The sampling valve as claimed in claim 7, wherein the second respective end of each arm of the yoke is engaged with a respective rotary part such that the yoke grips the rotary parts in such a way as to drive the rotary parts in rotation through a translational movement of the mobile part of the linear actuator.

9. The sampling valve as claimed in claim 1, wherein in at least one of the relative angular positions, at least one end stop defines the angular position of the external parts.

10. The sampling valve as claimed in claim 9, wherein the at least one end-stop comprises an end-stop element which extends axially into one external port in one of said external parts and another external port in a second external part, with an angular clearance about the axis of rotation (A).

11. The sampling valve as claimed in claim 1, wherein the external orifices, loops and ducts of the external parts, and the internal orifices passing through the internal part are configured so that, through their relative angular positions:
   in a sample-withdrawing state or rinsing state, several of said loops are connected, by several of said internal orifices of said internal part and several of said external orifices of said external parts, to at least one inlet duct and to at least one outlet duct; and
   in a dispensing state, at least one of said orifices of said internal part is a sampling chamber of calibrated volume and is directly connected, via at least one external orifices of said external parts, to at least one inlet duct and to at least one outlet duct.

12. The sampling valve as claimed in claim 11, wherein the external orifices, loops and ducts of the external parts, and the internal orifices passing through the internal part are configured so that, in a secondary dispensing state at least one of said internal orifices of said internal part is directly connected, via at least one of said external orifices of said external parts, to at least one inlet duct and to at least one outlet duct, said at least one of said internal orifices of said internal part being a sampling chamber of calibrated volume.

13. A device for analyzing biological parameters using at least one sampling valve as claimed in claim 1.

14. A sampling method involving use of a sampling valve as claimed in claim 1.

15. A sampling valve comprising two external parts, and one internal part clamped between said external parts wherein the external parts are rotatable about an axis of rotation (A), said internal part having opposite surfaces bearing in a fluid tight and sliding fashion against adjacent surfaces of said external parts, said external parts comprising a plurality of external orifices, loops and ducts, said loops and said ducts being configured to communicate selectively with internal orifices passing through said internal art, wherein the external orifices, loops, and the ducts of the external parts, and the internal orifices passing through the internal part are configured so that, through their relative angular positions:
- in a sample-withdrawing state or rinsing state, several of said loops are connected, by several of said internal orifices of said internal part and several of said external orifices of said external parts, to at least one inlet duct and to at least one outlet duct; and
- in at least one dispensing state, the series of loops are sampling loops of calibrated volume and are connected, each one separately, by several of said internal orifices of said internal part and several of said external orifices of said external parts, to at least one inlet duct and to at least one outlet duct.

16. The sampling valve as claimed in claim 15, wherein the external orifices, loops and ducts of the external parts, and the internal orifices passing through the internal part are configured so that, in a secondary dispensing state, a second series of said loops are sampling loops of calibrated volume, and
- are connected, each one separately, by several of said internal orifices of said internal part and several of said external orifices of said external parts, to at least one inlet duct and to at least one outlet duct.

17. The sampling valve as claimed in claim 16, wherein the external parts are able to be actuated selectively so that:
- said external parts move in opposite directions of rotation; or
- one of said external parts moves in a direction of rotation about the axis of rotation (A) and the other of said external parts does not move in rotation about said axis of rotation (A).

18. The sampling valve as claimed in claim 16, wherein the external orifices, loops and ducts of the external parts, and the internal orifices passing through the internal part are configured so as to define, through their relative angular positions:
- said sample-withdrawing state by way of a primary sample-withdrawing state, and also
- at least one of a secondary sample-withdrawing state and a secondary rinsing state, in which several of said loops, some of which are common to said loops of said primary sample-withdrawing state, are connected, by several of said internal orifices of said internal part and several of said external orifices of said external parts, to at least one inlet duct and to at least one outlet duct.

19. The sampling valve as claimed in claim 18, wherein the external parts are able to be actuated selectively so that:
- said external parts move in the same direction of rotation; or
- said external parts move in opposite directions of rotation; or
- one of said external parts moves in a direction of rotation about the axis of rotation (A) and the other of said external parts does not move in rotation about said axis of rotation (A).

20. The sampling valve as claimed in claim 1 wherein, in the dispensing state or, respectively, at least one of the dispensing states, at least one of the orifices of the internal part is connected directly, via external orifices of the external parts, to at least one inlet duct and to at least one outlet duct, and in which said at least one of said orifices of said internal part is a sampling chamber of calibrated volume.

21. A sampling valve comprising a first part, a second part, and one internal part sandwiched between the first part and second part, wherein at least one of the first and second parts are rotatable about a first axis of rotation from at least a first angular position to a second angular position with relation to the internal part, said internal part having a first surface that is slidably sealed against a first inner surface of the first part and a second surface that is slidably sealed against a first inner surface of the second part, wherein the first and second parts further comprise:
- a plurality of external orifices;
- a plurality of loops; and
- a plurality of ducts, wherein the plurality of loops and ducts are configured to selectively fluidly communicate with a plurality of internal orifices passing through the internal part, wherein in the first angular position, the sampling valve is in a sample-withdrawing or rinsing state, and in the second angular position the sampling valve is in a dispensing state, wherein the first inner surface of the first part and the first inner surface of the second part are devoid of any groove or trough for the transfer of fluid along a direction substantially perpendicular to the first axis.

* * * * *